United States Patent
E et al.

(10) Patent No.: US 6,849,291 B2
(45) Date of Patent: Feb. 1, 2005

(54) GAS SENSING ELEMENT AND METHOD FOR MANUFACTURING THE SAME

(75) Inventors: Gang E, Anjo (JP); Kiyomi Kobayashi, Kuwana (JP); Yasumichi Hotta, Mie-ken (JP); Namitsugu Fujii, Yokkaichi (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/271,534

(22) Filed: Oct. 17, 2002

(65) Prior Publication Data

US 2003/0057091 A1 Mar. 27, 2003

Related U.S. Application Data

(62) Division of application No. 09/922,716, filed on Aug. 7, 2001, now Pat. No. 6,478,941.

(30) Foreign Application Priority Data

Aug. 7, 2000 (JP) .................................. 2000-238723
May 1, 2001 (JP) .................................. 2001-134423

(51) Int. Cl.$^7$ ................................. B05D 5/12
(52) U.S. Cl. ............... 427/58; 427/123; 427/126.5; 427/304; 427/372.2; 427/443.1; 427/532; 427/554
(58) Field of Search ............... 427/58, 123, 126.5, 427/304, 372.2, 443.1, 532, 554

(56) References Cited

U.S. PATENT DOCUMENTS

| | | | |
|---|---|---|---|
| 4,107,018 A | * | 8/1978 | Bode et al. ............... 204/427 |
| 4,265,724 A | * | 5/1981 | Haecker et al. ............. 204/429 |
| 4,650,697 A | | 3/1987 | Kitagawa et al. |
| 4,828,673 A | * | 5/1989 | Maeda ....................... 204/427 |
| 5,077,270 A | | 12/1991 | Takeda et al. |
| 5,099,172 A | | 3/1992 | Taguchi et al. |
| 5,202,154 A | | 4/1993 | Matsuura et al. |
| 5,512,151 A | | 4/1996 | Hayamizu et al. |
| 5,767,036 A | * | 6/1998 | Freund et al. ............... 502/185 |
| 6,096,372 A | | 8/2000 | Nomura et al. |
| 6,254,926 B1 | * | 7/2001 | Katafuchi et al. .......... 427/125 |
| 6,326,098 B1 | | 12/2001 | Itoh et al. |

FOREIGN PATENT DOCUMENTS

| EP | 0513821 | 11/1992 |
|----|---------|---------|
| EP | 0686847 | 12/1995 |
| JP | 2-85756 | 3/1990 |
| JP | 5-77264 | 10/1993 |
| JP | 10-104194 | 4/1998 |

OTHER PUBLICATIONS

Patent Abstracts of Japan, vol. 013, No. 032 (P-817), Jan. 25, 1989 & JP 63 231255 A (NGK Spark Plug Co Ltd), Sep. 27, 1988.

* cited by examiner

*Primary Examiner*—Brian K. Talbot
(74) *Attorney, Agent, or Firm*—Nixon & Vanderhye P.C.

(57) ABSTRACT

A gas sensing element has a solid electrolytic body, a reference gas side electrode provided on a surface of the solid electrolytic body so as to be exposed to a reference gas, and a measured gas side electrode provided on another surface of the solid electrolytic body so as to be exposed to a measured gas. A crystal face strength ratio of the measured gas side electrode according to X-ray diffraction is $0.7 \leq \{I(200)/I(111)\}$ or $0.6 \leq \{I(220)/I(111)\}$.

6 Claims, 5 Drawing Sheets

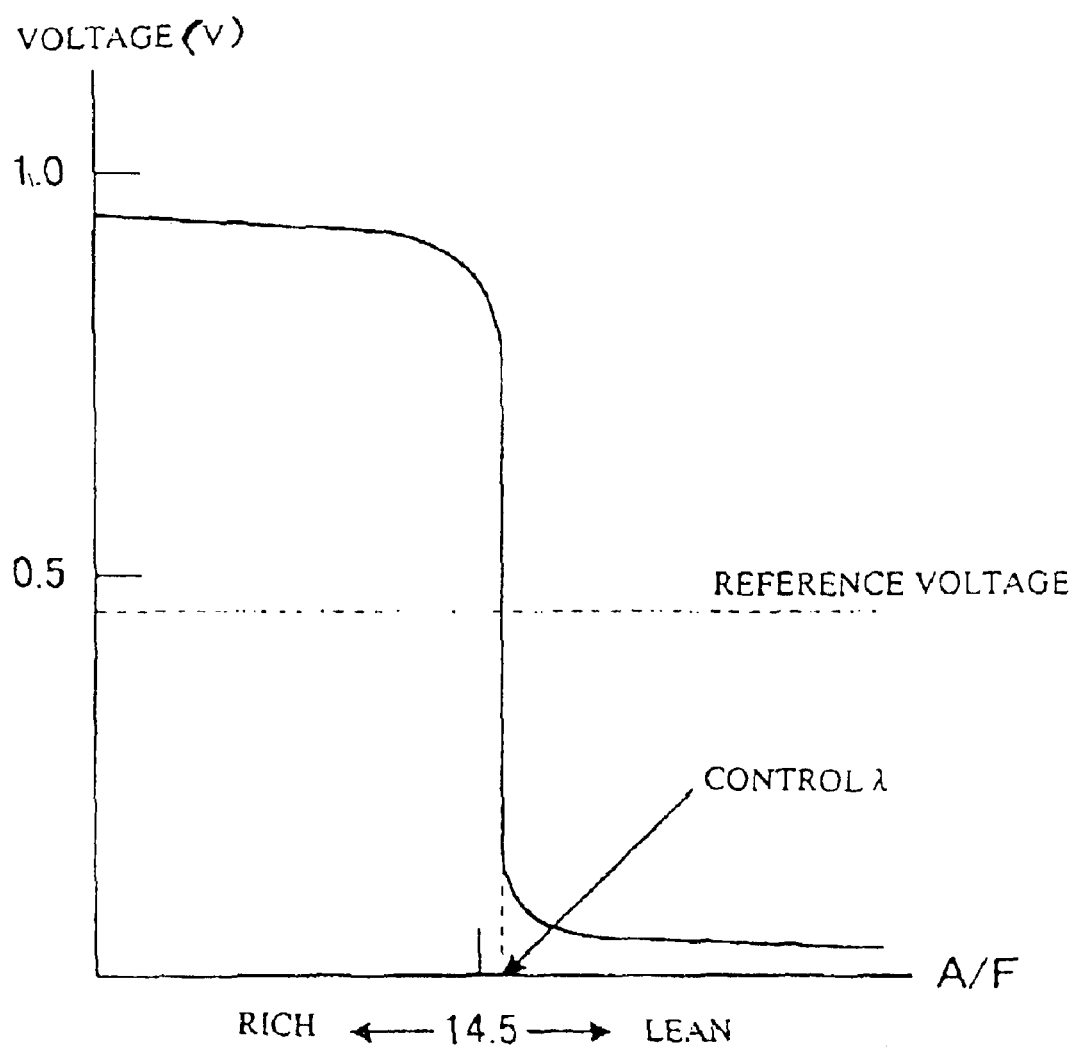

GAS SENSING ELEMENT AND METHOD FOR MANUFACTURING THE SAME

This application is a Division of Ser. No. 09/922,716 filed Aug. 7, 2001 now U.S. Pat. No. 6,478,941.

BACKGROUND OF THE INVENTION

The present invention relates to a gas sensor installed in an exhaust system of an automotive internal combustion engine to detect an oxygen concentration in the exhaust gas, or an air-fuel ratio, or the like.

The present invention relates to a gas sensing element used for controlling an air-fuel ratio of an internal combustion engine and a method for manufacturing the gas sensing element.

In general, to control the air-fuel ratio, a gas sensor is installed in an exhaust system of an automotive internal combustion engine.

The gas sensor comprises a gas sensing element provided at its front end for detecting an oxygen concentration. The gas sensing element comprises a solid electrolytic sintered body having oxygen ion conductance, a reference gas side electrode provided on a surface of the solid electrolytic body so as to be exposed to a reference gas, and a measured gas side electrode provided on another surface of the solid electrolytic body so as to be exposed to a measured gas. The measured gas side electrode is covered by a porous electrode protective layer.

In many cases, the electrode protective layer is a ceramic coating layer, or a double layer consisting of a ceramic coating layer and a γ-Al2O3 layer provided on this ceramic coating layer.

According to this type of gas sensing element, a measured gas reaches a measured gas side electrode through the ceramic coating layer or the double layer of the ceramic coating layer and the γ-Al2O3 layer. The bas sensing element produces a sensor output.

Recent radically changing circumstances, such as enhancement of emission control laws and regulations as well as requirements for high power internal combustion engines, has forced automotive manufacturers to develop automotive engines capable of precisely controlling combustion.

To realize this, it is essentially important to provide excellent gas sensors having sensing properties stable under severe operating conditions and durable for a long-term use.

FIG. 5 shows a characteristic curve representing a relationship between air-fuel ratio and voltage, as important sensor output characteristics of a gas sensing element used for combustion control of an internal combustion engine. In FIG. 5, point λ is referred to as a specific air-fuel ratio where the voltage undergoes steep changes. In FIG. 5, a reference voltage is a criteria used for judging whether a fuel injection amount should be increased or decreased in the combustion control of an internal combustion engine. In general, the reference voltage is set to 0.45V.

More specifically, when a sensor output is larger than the reference voltage, the fuel injection amount is reduced to form an air/fuel mixture whose air-fuel ratio is shifted to a lean side. On the contrary, when a sensor output is less than the reference voltage, the fuel injection amount is increased to form a relatively rich air/fuel mixture. Through such a feedback control, the air-fuel ratio of the controlled engine can be always kept in a window of a ternary catalyst.

Accordingly, to precisely perform the air-fuel ratio control, it is essentially important to stabilize the point λ (hereinafter, referred to as control λ).

In other words, the control λ should be stable during a long-term use of a gas sensing element and should be constant regardless of any environmental change of the gas sensing element.

When a gas sensing element is installed in an exhaust system of an internal combustion engine, a sensor output is produced in the following manner.

First, an exhaust gas containing unburnt components reaches a measured gas side electrode. Then, an equilibrium oxygen concentration is obtained through a catalytic reaction caused on the measured gas side electrode. The sensor output is produced as a signal representing a difference between the equilibrium oxygen concentration thus obtained and an oxygen concentration in the air serving as a reference gas.

Accordingly, it becomes possible to increase the measuring accuracy of a gas sensing element when an electrode having excellent activity is used as a measured gas side electrode of a gas sensing element.

The following is a method for activating a measured gas side electrode disclosed in Unexamined Japanese patent publication No. 10-104194.

First, a measured gas side electrode is formed on a surface of a solid electrolytic body by baking in the air at the temperature range from 1,000° C. to 1,400° C. Then, a heat treatment is applied to the measured gas side electrode thus formed in an atmosphere containing $H_2$.

Subsequently, a heat treatment in an inert atmosphere and a heat treatment in a non-oxidative atmosphere including moisture vapor are applied to the measured gas side electrode.

By combining these treatments, the catalytic activity of the measured gas side electrode can be enhanced.

However, according to the above-described conventional method, it was difficult to provide a gas sensing element having a measured gas side electrode which can assure a sufficiently stable control λ even in a severe high-temperature environment or in a poisonous environment containing Si compounds.

SUMMARY OF THE INVENTION

In view of the foregoing problems of the prior art, the present invention has an object to provide a gas sensing element capable of demonstrating excellent performances high temperature and/or Si poisoning environments.

To accomplish the above and other related objects, the present invention provides a first gas sensing element comprising a solid electrolytic body, a reference gas side electrode provided on a surface of the solid electrolytic body so as to be exposed to a reference gas, and a measured gas side electrode provided on another surface of the solid electrolytic body so as to be exposed to a measured gas, wherein a crystal face strength ratio of the measured gas side electrode according to X-ray diffraction is $0.7 \leq \{I(200)/I(111)\}$ or $0.6 \leq \{I(220)/I(111)\}$.

The first gas sensing element of the present invention is characterized in that the measured gas side electrode has a crystal face strength ratio according to X-ray diffraction satisfying the above-described conditions.

If $I(200)/I(111)$ is less than 0.7, a ratio of an active surface to an entire electrode surface will reduce to 0.5 or less and it will be difficult to assure satisfactory catalytic activity and stability for smoothly promoting an equilibrating reaction of exhaust gas.

If $I(220)/I(111)$ is less than 0.6, it will be difficult to assure satisfactory catalytic activity and stability.

To obtain crystal grains and an electrode film which are stable in energy level and easily fabricable, a preferable upper limit of the crystal face strength ratio is 1.0 in view of the fact that the total area of active faces (200) and (220) can be maximized and because according to this condition the crystal face orientation can satisfy the requirement that the solid electrolytic body causes no alteration.

Next, functions and effects of the present invention will be explained hereinafter.

Inventors of this invention enthusiastically conducted research and development for stabilizing the activity of a measured gas side electrode, i.e., stabilization of control λ. And, as a result of the research and development, the inventors have found the fact that a crystal face of the measured gas side electrode greatly contributes to activation and stability of a gas sensing element.

The measured gas side electrode is made of an electrode material containing noble metals which possess catalytic properties and usually have a face-centered cubic structure.

In a crystal lattice of such metals, specific crystal faces, i.e., faces (100) and (110), have a lower surface density of atoms compared with the other face (111) dominant in this crystal lattice.

Due to lower surface densities, these faces (100) and (110) promote adsorption of various exhaust components. Thus, these crystal faces can smoothly adsorb unburnt exhaust components and residual oxygen when the measured gas is exhaust gas. The equilibrating reaction smoothly advances.

According to the measured gas side electrode satisfying the above-described requirements, the faces (100) and (110) are orientated on the surface of the measured gas side electrode.

In the X-ray diffraction of a noble metal having a face-centered cubic structure, both faces (100) and (110) appear as faces (200) and (220) respectively. Hence, the strength ratio of this invention is expressed by using faces (200) and (220). Namely, strengths of faces (100) and (110) can be replaced by those of faces (200) and (220). The same result is obtained.

As described above, according to the gas sensing element of this invention, the entire surface of the measured gas side electrode possesses higher activity. Even when the measured gas side electrode is exposed to a severe high-temperature environment or in a poisoning environment containing Si components, the equilibrating reaction of exhaust gas can advance smoothly on the electrode surface. In this respect, the measured gas side electrode of this invention possesses excellent catalytic properties. Thus, it becomes possible to provides a sensor whose output is stable even after a long-term use in the high-temperature environment and which is robust against Si poisoning.

Accordingly, the gas sensing element of the present invention can maintain a stable control λ for a long time.

As apparent from the foregoing description, the present invention can provide a gas sensing element capable of demonstrating excellent performances in heat resistivity as well as in Si poisoning durability.

Furthermore, the present invention provides a second gas sensing element comprising a solid electrolytic body, a reference gas side electrode provided on a surface of the solid electrolytic body so as to be exposed to a reference gas, and a measured gas side electrode provided on another surface of the solid electrolytic body so as to be exposed to a measured gas, wherein a crystal face strength ratio of the measured gas side electrode according to X-ray diffraction is $1.3 \leq \{I(200)+I(220)\}/I(111)$.

The measured gas side electrode of this gas sensing element has a crystal face strength ratio according to X-ray diffraction satisfying the above-described conditions.

If the crystal face strength ratio is less than 1.3, activity of the measured gas side electrode will be soon worsened in severe operating conditions, such as a high-temperature environment and a Si poisoning environment. The control λ will vary widely depending on the operating conditions. Thus, the gas concentration cannot be measured accurately.

To obtain crystal grains and an electrode film which are stable in energy level and fabricable, a preferable upper limit of $\{I(200)+I(220)\}/I(111)$ is 2.0 in view of the fact that total area of faces (200) and (220) can be maximized and because this condition satisfies crystal face orientation requirement that the solid electrolytic body causes no alteration.

As described above, the measured gas side electrode is made of an electrode material containing noble metals which possess catalytic properties and usually have a face-centered cubic structure.

In a crystal lattice of such metals, both faces (100) and (110) have a lower surface density of atoms compared with other face (111) dominant in this crystal lattice.

Accordingly, these faces (100) and (110) promote adsorption of various exhaust components and act as active faces smoothly advancing the equilibrating reaction.

According to the measured gas side electrode satisfying the requirement $1.3 \leq \{I(200)+I(220)\}/I(111)$, the above-described active faces are orientated on the surface of the measured gas side electrode. Thus, it becomes possible to provides a sensor whose output is stable even after a long-term use in the high-temperature environment and robust against Si poisoning. Accordingly, the base sensing element of the present invention can maintain a stable control λ for a long time.

As apparent from the foregoing description, the present invention can provide a gas sensing element capable of demonstrating excellent performances in heat resistivity as well as in Si poisoning durability.

Furthermore, it is preferable that $\{I(200)+I(220)\}/I(111)$ is equal to or larger than 1.5.

With this arrangement, it becomes possible to easily form an electrode having a uniform film thickness and possessing stable and excellent catalytic activity without causing alteration of a solid electrolytic body.

The strength ratio of the above-described crystal faces can be obtained by measuring the X-ray diffraction strength of a surface of the measured gas side electrode (to be exposed to a measured gas) according to the X-ray diffraction method, for example by using a position sensitive proportional counter (PSPC) type microdiffractometer, manufactured by Rigaku Corporation. Alternatively, the crystal face strength ratio can be obtained according to another X-ray diffraction method using a similar diffractometer.

The following is an example of practical measurement.

According to the X-ray diffraction method using the above-described measuring apparatus, a thin X-ray with a diameter in the range from 200 μm to 300 μm with a power of 40 kV and 80 mA is irradiated onto a surface of the measured gas side electrode of each tested element piece (whose size is equal to or less than 5 mm) fixed by a sample holder.

Then, the strength ratio of crystal faces is calculated based on data collected simultaneously by a PSPC program (capable of performing both measurement and data processing) manufactured by Rigaku Corporation, while X-ray diffraction angle (2θ) varies in the range from 20° to 80°. This measurement is performed in the air at a room temperature. The measured data is subjected to correction based on a Si powder standard sample.

As described above, in the X-ray diffraction of a noble metal having a face-centered cubic structure, both faces (100) and (110) appear as faces (200) and (220) respectively. Hence, strengths of faces (100) and (110) can be replaced by those of faces (200) and (220) respectively.

When the noble metal having a face-centered cubic structure is random and does not have specific orientation, the strength ratio {I(200)+I(220)}/I(111) becomes 0.84.

Furthermore, the present invention provides a first method of manufacturing a gas sensing element comprising a solid electrolytic body, a reference gas side electrode provided on a surface of the solid electrolytic body so as to be exposed to a reference gas, and a measured gas side electrode provided on another surface of the solid electrolytic body so as to be exposed to a measured gas. The first manufacturing method comprises a step of providing a fine-grain nucleus (or a particulate core) of noble metal on an electrode forming portion of the solid electrolytic body, a step of applying a reducing heat treatment to the fine-grain nucleus, a step of forming a unbaked film electrode on the fine-grain nucleus, and a step of baking the film electrode in a reducing atmosphere to form the measured gas side electrode.

By utilizing the first manufacturing method of this invention, it becomes possible to form a measured gas side electrode from a fine-grain nucleus having active faces, such as faces (100) and (110), having lower surface densities of atoms.

According to the first manufacturing method, a fine-grain nucleus of noble metal is provided on an electrode forming portion (i.e., a portion where a measured gas side electrode is to be provided) of a solid electrolytic body. Then, a reducing heat treatment is applied to the fine-grain nucleus.

Grains of noble metal have higher surface energy. Applying a reducing heat treatment to a fine-grain nucleus induces chemical adsorption of reducing gas molecules in addition to thermal action.

As a result, active crystal faces having higher energy level, i.e., faces (100) and (110) having lower atomic surface densities, are formed on the fine-grain nucleus.

In a reducing atmosphere, the above-described active faces chiefly adsorb the molecules having strong reducing properties and higher activity, such as hydrogen molecules and carbon monoxide molecules. Growth of these active faces becomes slow compared with that of the other crystal face. As a result, the percentage of a crystal face (111) having a higher growth rate reduces and the active faces having slow growth rates remain in a wide region.

Therefore, in a case where an unbaked electrode film is formed on the fine-grain nucleus having active faces and this electrode film is baked in a reducing atmosphere, the orientation of the active faces can be maintained during the growth of the fine-grain nucleus. Thus, the electrode can be formed.

Accordingly, it becomes possible to obtain a gas sensing element having a measured gas side electrode on the surface of which active faces are orientated. The measured gas side electrode, when the active faces are dominant on the surface thereof, can produce a stable output even after a long-term use in the above-described high-temperature environment and can possess preferable durability against Si poisoning.

Accordingly, the gas sensing element of the present invention can maintain a stable control λ for a long time.

As apparent from the foregoing description, the present invention can provide a method for manufacturing a gas sensing element capable of demonstrating excellent performances in heat resistivity as well as in Si poisoning durability.

The above-described electrode film can be formed by utilizing chemical (i.e., electroless) plating, sputtering, vaporization etc.

A material can be used as the fine-grain nucleus when it includes at least one noble metal having a face-centered cubic structure such as Pt, Rh, Ir, Pd, Au etc.

The first manufacturing method of this invention can be put into practice in the following manner. First, a Pt nucleus is formed on a surface of a solid electrolytic body by reducing a chloroplatinic acid solution. Then, the Pt nucleus is subjected to the reducing thermal processing in a reducing atmosphere at a high temperature. Then, an electroless plating is applied to the Pt nucleus, thereby forming a plating layer on the Pt nucleus. Thereafter, the plating layer is thermally treated in a reducing atmosphere to form a measured gas side electrode.

It is preferable that the reducing heat treatment for the fine-grain nucleus is performed in the temperature range from 600° C. to 800° C.

If the temperature is less than 600° C., the effect of orientating the active faces on the fine-grain nucleus will be reduced. If the temperature is higher than 800° C., mutual bonding and grain growth will be caused between fine-grain nucleuses. No fine-grain nucleus may be formed on the electrode forming portion of a solid electrolytic body. The electrode film cannot be formed in an intended manner.

Furthermore, $H_2$—$N_2$ series atmosphere can be preferably used for the reducing heat treatment applied to the fine-grain nucleus according to this invention.

Hydrogen atoms are selectively adsorbed on faces (100) and (110) of the crystal lattice constituting the fine-grain nucleus. This promotes the formation of active faces.

Furthermore, it is preferable that the concentration of $H_2$ contained in the reducing heat treatment atmosphere is equal to or larger than 5 vol %.

If the $H_2$ concentration is less than 5 vol %, the active faces may not be formed due to lack of $H_2$ in the reducing heat treatment atmosphere.

Furthermore, the present invention provides a second method of manufacturing a gas sensing element comprising a solid electrolytic body, a reference gas side electrode provided on a surface of the solid electrolytic body so as to be exposed to a reference gas, and a measured gas side electrode provided on another surface of the solid electrolytic body so as to be exposed to a measured gas. The second manufacturing method comprises a step of providing a fine-grain nucleus of noble metal on an electrode forming portion of the solid electrolytic body, a step of irradiating a laser beam to the fine-grain nucleus, a step of forming a unbaked electrode film on the fine-grain nucleus, and a step of baking the electrode film in a reducing atmosphere to form the measured gas side electrode.

Like the above-described reducing heat treatment, performing the laser irradiating processing is effective to activate and rearrange the surficial atoms of the fine-grain nucleus. Accordingly, it becomes possible to obtain a gas sensing element having a measured gas side electrode on the surface of which active faces are orientated. The measured gas side electrode, when the active faces are dominant on the surface thereof, can produce a stable output even after a long-term use in the above-described high-temperature environment and can possess preferable durability against Si poisoning. Accordingly, the gas sensing element of the present invention can maintain a stable control λ for a long time.

As apparent from the foregoing description, the present invention can provide a method for manufacturing a gas sensing element capable of demonstrating excellent performances in heat resistivity as well as in Si poisoning durability.

The second manufacturing method of this invention can be put into practice in the following manner. First, a Pt nucleus is formed by reducing a chloroplatinic acid solution and is subjected to the laser irradiation processing. Thereafter, an electroless plating is applied to the Pt nucleus, thereby forming a plating layer comprising a Pt grain polycrystal having excellent orientation.

Then, the Pt plating later is baked in an inert atmosphere to obtain a measured gas side electrode having excellent orientation.

Regarding the laser irradiation, a preferable laser power is in the range from 10 mW to 50 mW and a preferable irradiation time is in the range from 1 minute to 30 minutes.

When the laser irradiation is performed within the above irradiation time, increasing the laser power up to 50 mW will give a significant damage to a solid electrolytic body and accordingly will cause local alterations on the solid electrolytic body (i.e., black spots).

Furthermore, if the irradiation time exceeds 30 minutes, the fine-grain nucleus will agglutinate or partly evaporate. The electrode film thus formed will not have a uniform film thickness.

If the laser power is less than 10 mW, or if the irradiation time is shorter than 1 minute, no orientation will be caused on the fine-grain nucleus. The effects of the present invention will not be obtained.

Furthermore, the present invention provides a third method of manufacturing a gas sensing element comprising a solid electrolytic body, a reference gas side electrode provided on a surface of the solid electrolytic body so as to be exposed to a reference gas, and a measured gas side electrode provided on another surface of the solid electrolytic body so as to be exposed to a measured gas. The third manufacturing method comprises a step of preparing a paste of fine-grain nucleus of noble metal applied crystal face orientation processing beforehand, a step of forming a unbaked electrode film by coating the paste on an electrode forming portion of the solid electrolytic body, and a step of baking the electrode film in a reducing atmosphere to form the measured gas side electrode.

Orientating crystal faces of the fine-grain nucleus of noble metal makes it possible to form the active faces, i.e., faces (100) and (110), having higher energy levels.

According to the present invention, a paste is prepared so as to include the fine-grain nucleus of noble metal applied to the crystal face orientation processing beforehand. Then, an electrode film is formed by using this paste. Then, a reducing heat treatment is applied. The fine-grain nucleus grows while maintaining the orientation of the active faces.

Accordingly, as the electrode film is formed and baked while maintaining the orientation adequately, it becomes possible to obtain a gas sensing element having a measured gas side electrode on the surface of which active faces are orientated.

As described above, the measured gas side electrode can produce a stable output even after a long-term use in the above-described high-temperature environment and can possess preferable durability against Si poisoning. Accordingly, the gas sensing element of the present invention can maintain a stable control λ for a long time.

As apparent from the foregoing description, the present invention can provide a method for manufacturing a gas sensing element capable of demonstrating excellent performances in heat resistivity as well as in Si poisoning durability.

The third manufacturing method of this invention can be put into practice in the following manner.

First, a chloroplatinic acid is thermally decomposed in an inert atmosphere at the temperature range from 1,000° C. to 1,100° C. to obtain a Pt nucleus with active faces having excellent orientation. The Pt nucleus thus obtained is mixed with a binder and the like to form a paste. Then, the paste is baked in an inert gas atmosphere to obtain a measured gas side electrode whose active faces have excellent orientation.

Furthermore, in any of the above-described manufacturing methods of the present invention, a preferable baking temperature in a reducing atmosphere is in the range from 1,000° C. to 1,100° C.

The measured gas side electrode baked in this temperature range has numerous micro pores which can enhance gas diffusing performance. Furthermore, it becomes possible to improve the response of sensor output.

If the baking temperature exceeds 1,100° C., alteration of a solid electrolytic body will be caused.

Application of the present invention is not limited to a cup-shaped gas sensing element (refer to FIGS. 1 and 2). Therefore, the present invention can be applied to another type of gas sensing elements, such as a multilayered planar gas sensing element consisting of a planar solid electrolytic body, a planar measured gas side electrode or the like stacked successively.

Furthermore, application of the present invention is not limited to an oxygen concentration cell type element. Therefore, the present invention can be applied to another type of gas sensing elements, such as a limit-current type element, a lean sensor type element, and an air-fuel ratio sensing element.

Furthermore, the gas sensor of the present invention can be used as a NOx sensor, a HC sensor, or a CO sensor.

BRIEF DESCRIPTION OF THE DRAWINGS

The above and other objects, features and advantages of the present invention will become more apparent from the following detailed description, which is to be read in conjunction with the accompanying drawings, in which:

FIG. 5 is a graph showing a relationship between air-fuel ratio and voltage of a conventional gas sensing element.

DESCRIPTION OF THE PREFERRED EMBODIMENTS

Figure 1:
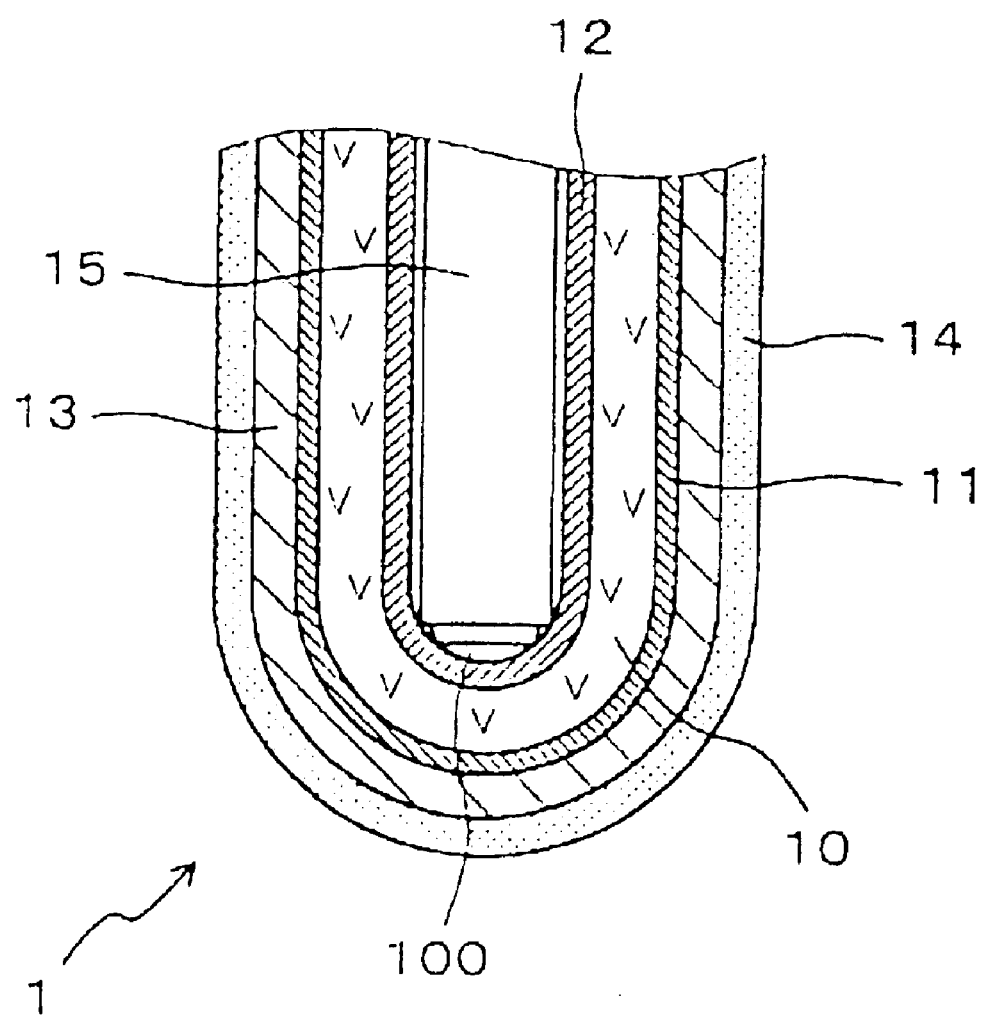
FIG. 1 is a cross-sectional view showing an essential arrangement of a gas sensing element in accordance with a preferred embodiment of the present invention.

Preferred embodiments of the present invention will be explained hereinafter with reference to attached drawings. Identical parts are denoted by the same reference numerals throughout drawings.

Gas Sensing Element

Hereinafter, a gas sensing element according to a preferred embodiment of the present invention will be explained with reference to FIGS. 1, 2 and 5.

As shown in FIG. 1, the gas sensing element of the preferred embodiment comprises a solid electrolytic body 10, a reference gas side electrode 12 provided on a surface of the solid electrolytic body 10 so as to be exposed to a reference gas, and a measured gas side electrode 11 provided on another surface of the solid electrolytic body 10 so as to be exposed to a measured gas.

A crystal face strength ratio of the measured gas side electrode 11 according to X-ray diffraction is $1.3 \leq \{I(200)+I(220)\}/I(111)$.

The gas sensing element 1 of this embodiment is incorporated in a gas sensor 9 shown in FIG. 2 which is later described. The gas sensor 9 is installed in an exhaust gas system of an automotive vehicle to control the combustion of an internal combustion engine.

The gas sensing element 1 comprises a solid electrolytic body having an oxygen ionic conductance. Two electrodes are provided on opposite surfaces of the solid electrolytic body so as to cooperatively constitute an electrochemical cell. A measured gas (exhaust gas) is introduced in the vicinity of one electrode. A reference gas (air) is introduced in the vicinity of the other electrode. An electric potential difference, representing an oxygen concentration difference between the reference gas and the measured gas, is produced between two electrodes. In this respect, the gas sensing element 1 is a cell producing an electromotive force representing an air-fuel ratio of the measured gas.

As shown in FIG. 1, the solid electrolytic body 10 has a cup-shaped configuration defining therein a reference gas chamber 100 into which the air is introduced. The reference gas side electrode 12 is provided on an inner surface of the solid electrolytic body 10 so that the reference gas side electrode 12 is exposed to the reference gas stored in the reference gas chamber 100. The measured gas side electrode 11 is provided on an outer surface of the solid electrolytic body 10.

The outer surface of the measured gas side electrode 11 is covered by a first protective layer 13 which suppresses the diffusion of measured gas. A second protective layer 14, serving as a trapping layer, covers the outer surface of the first protective layer 13.

A rodlike ceramic heater 15 is disposed in the reference gas chamber 100. A front end of heater 15 is brought into contact with the bottom of the reference gas chamber 100.

The gas sensing element 1 has above-described characteristics of FIG. 5 showing the relationship between voltage and air/fuel ratio, according to which a control λ indicates a steep change point in the voltage. In FIG. 5, a reference voltage is a criteria used for judging whether a fuel injection amount should be increased or decreased in the combustion control of an internal combustion engine. In general, the reference voltage is set to 0.45 V.

Manufacturing Method (I)

The measured gas side electrode is manufactured in the following manner by using a regular sintering process.

First, a solid electrolytic body is cleaned. Then, to form a Pt nucleus, a solution containing 5 wt % chloroplatinic acid and a reducing solution containing 10 wt % sodium tetrahydroborate are sprayed onto an electrode forming portion where a measured gas side electrode is to be provided. The Pt nucleus becomes a fine-grain nucleus (or a particulate core) of noble metal.

The solid electrolytic body with the fine-grain nucleus thus formed is cleaned in distilled water and then dried.

Next, the fine-grain nucleus is subjected to a two-hour reducing heat treatment at a temperature range from 500° C. to 800° C. in a reducing atmosphere consisting of 5 vol % $H_2$ and 95 vol % $N_2$ or in a reducing atmosphere consisting of 20 vol % $H_2$ and 80 vol % $O_2$.

Thereafter, an electroless plating is applied to the Pt nucleus to form a plating layer serving as a unbaked electrode film. Furthermore, the unbaked electrode film is baked in a reducing atmosphere to obtain a measured gas side electrode.

In this case, the heat treatment conditions for the electrode film are as follows. The heat treatment was performed for one hour at the temperature of 1,100° C. in a reducing atmosphere consisting of 20 vol % $H_2$ and 80 vol % $N_2$.

Gas Sensor Arrangement

The gas sensor 9 will be explained hereinafter.

Figure 2:
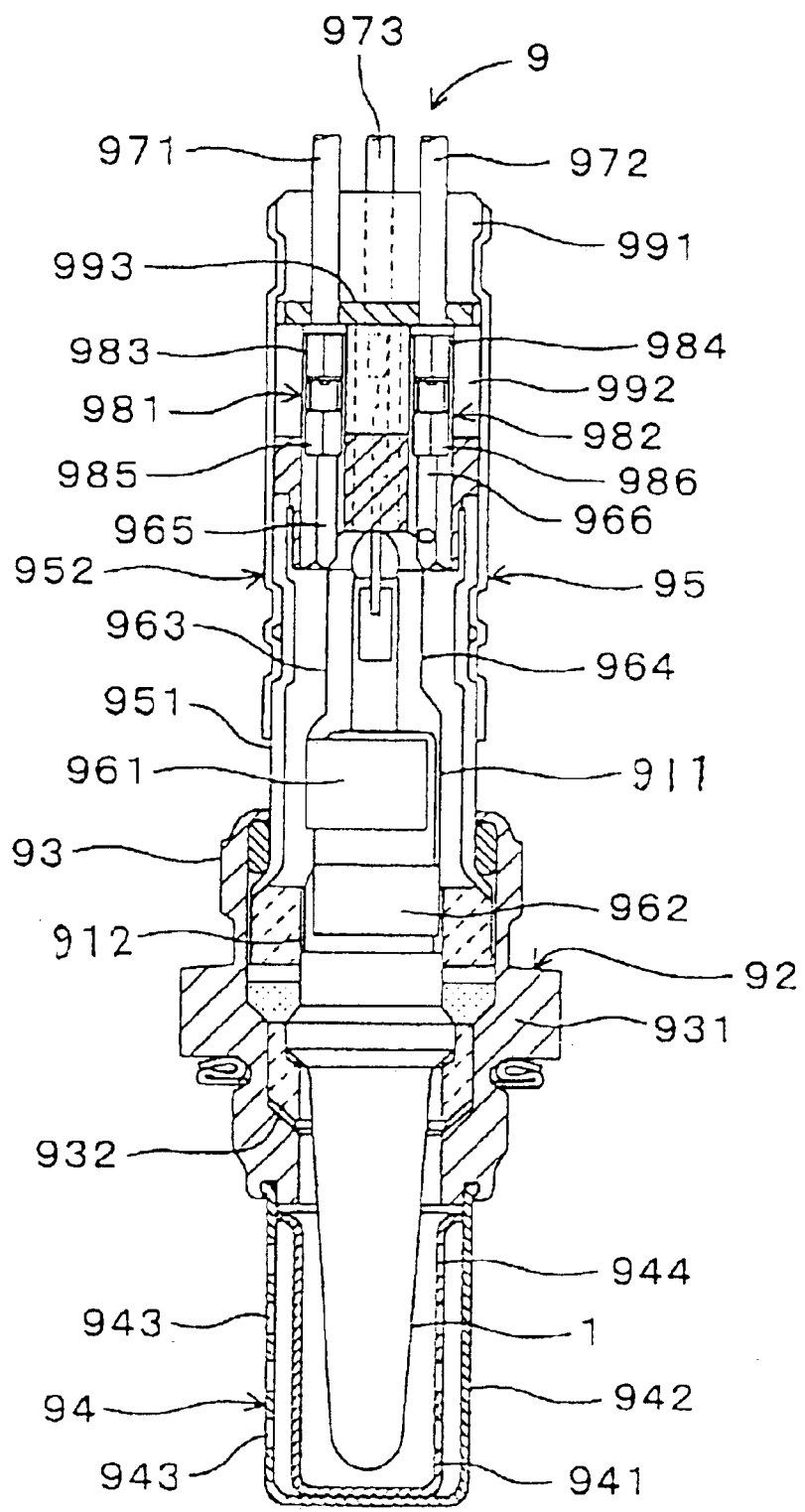
FIG. 2 is a cross-sectional view showing a gas sensor in accordance with the preferred embodiment of the present invention.

FIG. 2 shows the gas sensor 9 incorporating a gas sensing element 1.

In addition to the gas sensing element 1, the gas sensor 9 has a housing 92 accommodating the gas sensing element 1.

The housing 92 has a barrel portion 93 with a flange 931 formed at the center thereof. A measured gas side cover 94, to be placed in an exhaust gas passage of an exhaust gas system, is connected to a distal end of the barrel portion 93. An air side cover 95, to be exposed to the air, is connected to a distal end of the barrel portion 93.

The measured gas side cover 94 consists of an inner cover 941 and an outer cover 942 which are made of stainless steel and cooperatively constitute a double-layer construction. These covers 941 and 942 have a plurality of holes 943 and 944 opened to introduce the exhaust gas into the measured gas side cover 94.

On the other hand, the air side cover 95 comprises a main cover 951 attached at one end to the barrel portion 93 and a sub cover 952 overlapping with the other end of the main cover 951. These covers 951 and 952 have holes for introducing air into the air cover 95.

The gas sensing element 1 is supported through an insulating member 932 by the inside surface of the barrel portion 93. A metallic plate terminal 961 is connected to the reference gas side electrode 12 of the gas sensing element 1 via a lead 911 and another metallic plate terminal 962 is connected to the measured gas side electrode 11 of the gas sensing element 1 via a lead 912 in such a manner that the electrode leads 911 and 912 are surrounded and clamped by the metallic plate terminals 961 and 962.

The plate terminals 961 and 962 are connected to output lead wires 971 and 972. More specifically, belt-like terminal pieces 963 and 964 protrude from the plate terminals 961 and 962 toward contact pieces 965 and 966, respectively.

The terminal pieces 963 and 964 are connected to lower ends 985 and 986 of connectors 981 and 982. The other ends 983 and 984 of the connectors 981 and 982 are connected to the output lead wires 971 and 972.

The plate terminals 961 and 962 are respectively formed by deforming an inverse T-shaped metallic plate into a cylindrical shape so as to hold the lead 911 of reference gas side electrode 12 and the lead 912 of measured gas side electrode 11.

An elastic spring force of the metallic plate gives an adequate pressing force for clamping the electrode leads 911 and 912 by the plate terminals 961 and 962.

The lead wires 971 and 972 are respectively subjected to a tensile force acting in an axial direction of the gas sensor 9. Thus, the lead wires 971 and 972 may pull the plate terminals 961 and 962 via the connectors 981 and 982, respectively. Thus, the plate terminals 961 and 962 may slide in the axial direction.

A stopper 993, sandwiched between rubber bushes 991 and 992, is provided at the proximal end of the gas sensor 9 to restrict the sliding of the plate terminals 961 and 962. The stopper 993, also preventing the shifting of connectors 981 and 982, is a resin-made member capable of insulating the lead wires 971 and 972 from each other.

A wire 973 supplies electric power to the heater 15 of the gas sensing element 1. The gas sensor 9 is fixed at the flange 931 to the wall of the exhaust passage so that the measured gas side cover 94 protrudes in the exhaust gas passage.

Hereinafter, functions and effects of this embodiment will be explained.

The measured gas side electrode is constituted by Pt which possesses catalytic properties and has a face-centered cubic structure. In the crystal lattice of Pt, crystal faces (100) and (110) have a lower surface density of atoms and higher activity compared with other face (111) dominant in this crystal lattice.

Accordingly, when the measured gas side electrode satisfies the above-described condition that {I(200)+I(220)}/I(111) is equal to or larger than 1.3, the crystal face having higher activity, i.e., an active surface, is orientated on the surface of the measured gas side electrode. Thus, even when the gas sensor is exposed to a high-temperature environment for a long time, the gas sensor can produce a stable output. The gas sensor becomes robust against Si poisoning and can maintain a stable control λ for a long time.

As described above, this embodiment can provide a gas sensing element which is excellent in heat resistance as well as in Si poisoning durability.

Performance of a gas sensing element having a measured gas side electrode of the present invention was evaluated through the following measurement.

A total of eight gas sensing elements ware prepared as test samples (refer to Table 1). The measured gas side electrode of each test sample was manufactured according the above-described first manufacturing method. As apparent from Table 1, the manufactured gas sensing elements were respectively differentiated in the conditions of a heat treatment applied to the Pt nucleus serving as a fine-grain nucleus of noble metal. The reducing heat treatment for each tested gas sensing element was conducted for two hours.

For comparison, reference sample I was prepared as a gas sensing element having not been subjected to the reducing heat treatment for the Pt nucleus. The measured gas side electrode of reference sample I was manufactured by directly applying the electroless plating to form a plating layer of the electrode film and then baking the electrode film in a reducing atmosphere. In this case, the baking processing was performed for one hour at the temperature of 1,100° C. in a reducing atmosphere containing 20 vol % $H_2$.

Manufacturing Method (II)

A second manufacturing method differs from the above-described first manufacturing method in a step of applying laser irradiation processing to a fine-grain nucleus of noble metal provided in an electrode forming portion.

After applying the activation processing using chloroplatinic acid like the above-described example 1, a ultraviolet laser beam with a diameter of 5 mm was irradiated entirely to the fine-grain nucleus for 30 minutes while the laser output was changed in a range from 1 mW to 50 mW. The laser beam irradiation was performed in an atmosphere consisting of 20 vol % $H_2$ and 80 vol % $O_2$. As a result of laser beam irradiation, the surficial atoms of the fine-grain nucleus were reorientated so as to form the faces (100) and (110).

Like the first manufacturing method, an electroless plating was applied to form a plating layer of a unbaked electrode film. The electrode film was baked in a reducing atmosphere to form a measured gas side electrode.

In this case, the baking processing was performed for one hour at the temperature of 1,100° C. in a reducing atmosphere consisting of 20 vol % $H_2$ and 80 vol % $N_2$.

Reference sample II was prepared as a gas sensing element fabricated from a fine-grain nucleus having not been subjected to the laser irradiation.

Manufacturing Method (III)

A third manufacturing method differs from the above-described first manufacturing method by steps of preparing a paste of a fine-grain nucleus applied the crystal face orientation processing beforehand and then forming a unbaked electrode film resulting from this paste.

First, chloroplatinic acid powder was subjected to a heat decomposition within a temperature range from 600° C. to 1,000° C. in a reducing atmosphere containing 20 vol % $H_2$, thereby obtaining a fine-grain nucleus of platinum having a grain size of several hundreds Å with faces (100) and (110) orientated on the surface thereof.

Next, a paste was formed by uniformly kneading the above-described platinum fine-grain nucleus (70 wt %) with 5 wt % binder made of PVB (polyvinyl butyral), 23 wt % terpineol solvent, and 2 wt % glass frit.

The paste was coated on an electrode forming portion by using a conventionally known technique such as a screen printing or a roll printing. After the paste having been applied to the electrode forming portion was dried, binder removing processing was performed in the air for one hour at the temperature of 600° C., thereby obtaining an electrode film.

Thereafter, like the first manufacturing method, the electrode film was baked in a reducing atmosphere to form a measured gas side electrode.

In this case, the heat treatment of the electrode film was performed for two hours at the temperature of 1,100° C. in a reducing atmosphere consisting of 20 vol % $H_2$ and 80 vol % $N_2$.

Reference sample III was prepared as a gas sensing element fabricated without applying the reducing heat treatment to the Pt nucleus.

Measurement of Crystal Face Strength Ratio

A measurement of crystal face strength ratio was performed on respective measured gas side electrodes of the gas sensing elements manufactured according to the above-described first to third manufacturing methods.

A position sensitive proportional counter (PSPC) type microdiffractometer, manufactured by Rigaku Corporation, was used to measure an X-ray diffraction strength at three arbitrary points on a surface of each measured gas side electrode according to the X-ray diffraction method.

From this measurement result, a value of {I(200)+I(220)/I(111)} was calculated. An average of measured values at the three arbitrary points was obtained as the crystal face strength ratio as shown in Tables 1 to 3.

The conditions for measuring the X-ray diffraction strength was as follows. A thin X-ray with a diameter in the range from 200 μm to 300 μm with a power of 40 kV and 80 mA was irradiated onto a surface of the measured gas side electrode of each tested element piece (whose size is equal to or less than 5 mm) fixed by the sample holder.

Then, the strength ratio of crystal faces was calculated based on data collected simultaneously by the PSPC program (capable of performing both measurement and data processing) while an X-ray diffraction angle (2θ) varied in the range from 20° to 80°. This measurement was performed in the air at a room temperature. The measured data was subjected to correction based on a Si powder standard sample.

Figure 3:
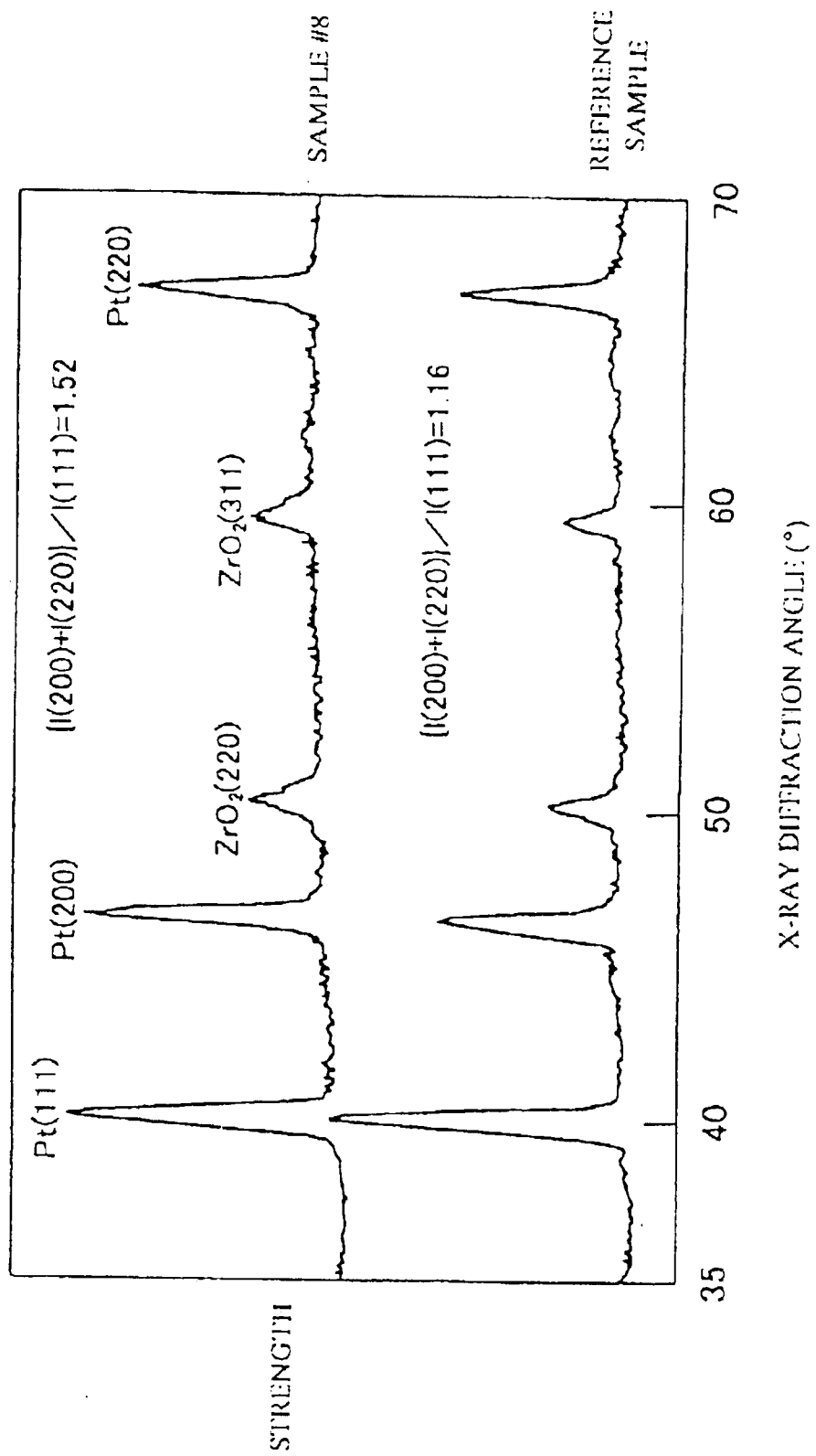
FIG. 3 is a graph showing a relationship between X-ray diffraction angle and diffraction strength with respect to each of sample 8 and a reference sample in accordance with the preferred embodiment of the present invention.

FIG. 3 is a graph showing a relationship between X-ray diffraction strength and diffraction angle with respect to each of sample 8 and the reference sample. The X-ray diffraction strength measurement was conducted on a measured gas side electrode provided on a surface of the solid electrolytic body. As apparent from FIG. 3, an X-ray strength curve of this invention includes several peaks inherent to the electrode itself and peaks resulting from $ZrO_2$ contained in a solid electrolytic body because the X-ray is irradiated onto the measured gas side electrode provided on a surface of the solid electrolytic body.

In the graph, the leftmost peak is resultant from Pt (111), i.e., a crystal lattice (111) of Pt. Other peaks successively aligning in the rightward direction are resultant from Pt(200), $ZrO_2$(220), $ZrO_2$(311), and Pt(220).

The following formula defines a crystal face strength ratio.

$$\{I(200)+I(220)\}/I(111)$$

where I(200), I(220), and I(111) represent height values of respective peaks Pt(200), Pt(220) and Pt(111).

Measurement of Control λ

Next, measurement of control λ will be explained.

Each gas sensing element was incorporated in the gas sensor 9 shown in FIG. 2. The gas sensor 9 was installed in an exhaust pipe of a 2,000 cc gasoline engine. The engine was driven. The exhaust gas temperature was increased to 600° C., while temperature of the gas sensing element was increased up to 700° C. due to heating by its built-in heater. Under this condition, a self feedback control of the engine was performed.

At this moment, an air-fuel ratio of the exhaust gas was accurately measured by an A/F sensor installed in the same exhaust pipe where the tested gas sensor was installed.

A measured A/F value at each measurement time was adopted as an accurate control λ which is referred to as λ0. A control λ obtained from each gas sensing element was referred to as λ1. A ratio of both values, i.e., λ1/λ0, represents a change rate of control λ as shown in Table 1.

The high-temperature durability was measured in the following manner.

Each tested gas sensing element was exposed to an exhaust gas of 1,000° C. for 500 hours. Thereafter, a control λ was evaluated in the same manner as described above. A change rate of control λ before and after the high-temperature durability test was measured.

The Si poisoning durability was measured in the following manner.

An in-line four cylinder engine of 2,000 cc equipped with a fuel injector was continuously driven at 3,000 rpm, while the temperature of the tested sensing element was kept at 600° C. through heating by a heater. The gasoline used for this durability test contains Si oil (methyldisiloxane) of 0.5 cc per liter. The durability test was conducted for 200 hours.

In this condition, the engine was driven for 200 hours to sufficiently expose the gas sensing element to a Si poisoning environment.

Like the high-temperature durability test, a change rate of control λ before and after the Si poisoning durability test was measured.

In each table, a sample indicated by ⊙ has shown a change rate less than 0.1%. A sample indicated by ○ has shown a change rate in the range from 0.1% to 0.3%. A sample indicated by Δ has shown a change rate in the range from 0.3% to 0.4%. A sample indicated by × has shown a change rate equal to or larger than 0.4%.

The tested samples 2, 3, 4, 6, 7, 8, 11, 12, 13, 14, 16 and 17 according to the present invention, whose crystal face strength being equal to or larger than 1.3, have showed preferable results in both of high-temperature durability and Si poisoning durability (indicated by ⊙ or ○ in the evaluation).

On the other hand, other samples 1, 5, 9, 10, 15 and reference samples I to III could not obtain satisfactory results in their performances.

From Table I, preferable conditions for the reducing heat treatment applied to the fine-grain nucleus are derived as follows.

More specifically, a reducing heat treatment is preferably performed at a temperature range from 600° C. to 800° C. in a reducing atmosphere containing $H_2$ whose concentration is equal to or larger than 20 vol %. In other words, it is understood that performing a reducing heat treatment in this temperature range with this hydrogen concentration ensures to obtain a crystal face strength ratio equal to or larger than 1.30.

It is also understood that the crystal face strength ratio equal to or larger than 1.30 cannot be obtained when no reducing heat treatment is applied to a Pt nucleus (refer to the reference sample I).

From Table II, it is understood that application of laser irradiation is effective to reduce a change rate of control λ in both of the high-temperature durability test and the poisoning durability test. Thus, the application of laser irradiation leads to improvement of durability.

The tested samples 9 and 10, each having a lower crystal face strength ratio, could not show satisfactory performance although their change rates were lower than that of the reference sample II. From this fact, it is understood that insufficient laser irradiation leads to dissatisfactory performance.

Accordingly, the test result of Table 2 reveals that the laser irradiation brings preferable result when the laser power is equal to or larger than 10 mW.

From Table III, it is understood that forming an electrode by using a paste containing a fine-grain nucleus applied the crystal face orientation processing beforehand is effective to reduce a change rate of control λ in both of the high-temperature durability test and the poisoning durability test.

Figure 4:
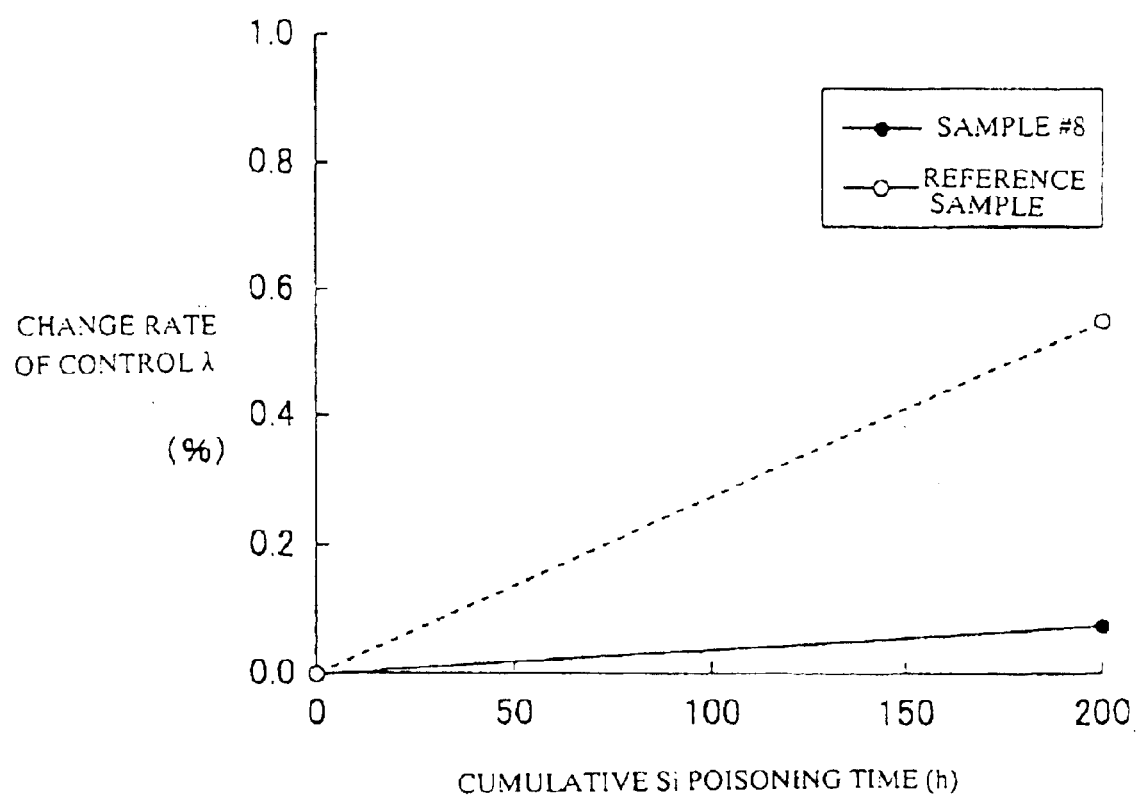
FIG. 4 is a graph showing a relationship between cumulative Si poisoning time and change rate of control λ with respect to each of sample 8 and the reference sample in accordance with the preferred embodiment of the present invention.

As apparent from FIG. 4, the control λ of sample 8 showed a dull change as sample 8 has a crystal face strength rate equal to or larger than 1.3. On the contrary, the control λ of the reference sample showed a steep change as the reference sample has a lower crystal face strength.

TABLE 1

| | reducing heat treatment conditions | | crystal face strength ratio {I(200) + I(220)}/I(111) | I(200)/I(111) | I(220)/I(111) | change rate of control λ in high-temp durability test (%) | | change rate of control λ in Si poisoning durability test (%) | |
|---|---|---|---|---|---|---|---|---|---|
| sample #1 | 500° C.~ | 5 vol % | 1.20 | 0.65 | 0.55 | 0.43 | X | 0.46 | X |
| sample #2 | 600° C.~ | H2 + | 1.30 | 0.70 | 0.60 | 0.17 | ○ | 0.28 | ○ |
| sample #3 | 700° C.~ | 95 vol % | 1.39 | 0.76 | 0.63 | 0.14 | ○ | 0.18 | ○ |
| sample #4 | 800° C.~ | N2 | 1.48 | 0.83 | 0.65 | 0.10 | ○ | 0.11 | ○ |
| sample #5 | 500° C.~ | 20 vol % | 1.25 | 0.71 | 0.54 | 0.30 | Δ | 0.34 | Δ |
| sample #6 | 600° C.~ | H2 + | 1.38 | 0.75 | 0.63 | 0.14 | ○ | 0.20 | ○ |
| sample #7 | 700° C.~ | 80 vol % | 1.45 | 0.82 | 0.63 | 0.07 | ◎ | 0.14 | ○ |
| sample #8 | 800° C.~ | N2 | 1.52 | 0.85 | 0.67 | 0.00 | ◎ | 0.08 | ◎ |
| reference sample I | | | 1.16 | 0.62 | 0.54 | 0.46 | X | 0.55 | X |

TABLE 2

| | laser irradiation conditions | crystal face strength ratio {I(200) + I(220)}/I(111) | I(200)/I(111) | I(220)/I(111) | change rate of control λ in high-temp durability test (%) | | change rate of control λ in Si poisoning durability test (%) | |
|---|---|---|---|---|---|---|---|---|
| sample #9 | 1 mW | 1.24 | 0.63 | 0.61 | 0.34 | Δ | 0.41 | X |
| sample #10 | 5 mW | 1.27 | 0.65 | 0.62 | 0.30 | Δ | 0.34 | Δ |
| sample #11 | 10 mW | 1.30 | 0.70 | 0.60 | 0.20 | ○ | 0.28 | ○ |
| sample #12 | 20 mW | 1.36 | 0.74 | 0.62 | 0.14 | ○ | 0.20 | ○ |
| sample #13 | 30 mW | 1.44 | 0.78 | 0.66 | 0.08 | ◎ | 0.14 | ○ |
| sample #14 | 50 mW | 1.50 | 0.85 | 0.65 | 0.07 | ◎ | 0.07 | ◎ |
| reference sample II | | 1.16 | 0.62 | 0.54 | 0.46 | X | 0.55 | X |

TABLE 3

| | cyrstal face orientation processing | crystal face strength ratio {I(200) + I(220)}/I(111) | I(200)/I(111) | I(220)/I(111) | change rate of control λ in high-temp durability test (%) | | change rate of control λ in Si poisoning durability test (%) | |
|---|---|---|---|---|---|---|---|---|
| sample #15 | 600° C. | 1.25 | 0.64 | 0.61 | 0.34 | Δ | 0.41 | X |
| sample #16 | 800° C. | 1.34 | 0.72 | 0.62 | 0.14 | ○ | 0.20 | ○ |
| sample #17 | 1000° C. | 1.42 | 0.77 | 0.65 | 0.08 | ◎ | 0.20 | ○ |
| reference sample III | | 1.08 | 0.56 | 0.42 | 0.51 | X | 0.60 | X |

Thus, the application of laser irradiation leads to improvement of durability.

The tested sample 15, having a lower crystal face strength ratio, could not show satisfactory performance although its change rate was lower than that of the reference sample III. From this fact, it is understood that lower temperature during the crystal face orientation processing leads to dissatisfactory performance.

Accordingly, the test result of Table 3 reveals that applying the reducing heat treatment as crystal face orientation processing brings preferable result when the temperature during the reducing heat treatment is equal to or larger than 800° C.

FIG. 4 shows a relationship between cumulative Si poisoning time and change rate of control λ with respect to each of the tested sample 8 and the reference sample.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A method of manufacturing a gas sensing element comprising a solid electrolytic body, a reference gas side electrode provided on a surface of said solid electrolytic body so as to be exposed to a reference gas, and a measured gas side electrode provided on another surface of said solid electrolytic body so as to be exposed to a measured gas, said manufacturing method comprising:

providing a fine-grain nucleus of noble metal on an electrode forming portion of said solid electrolytic body;

applying a reducing heat treatment to said fine-grain nucleus;

forming an unbaked film electrode on said fine-grain nucleus; and baking said film electrode in a reducing atmosphere to form said measured gas side electrode thereby providing a crystal face strength ratio of said measured gas side electrode according to X-ray diffraction satisfies the following relationship $$0.7 \leq \{I(200)/I(111)\} \text{ or } 0.61 \leq \{I(220)/I(111)\}$$

where I(200) represents the intensity of an X-ray diffraction measurement for a crystal face (200) of said measured gas side electrode, I(111) represents the intensity of an X-ray diffraction measurement for a crystal face (111) of said measured gas side electrode and I(220) represents the intensity of an X-ray diffraction measurement for a crystal face (220) of said measured gas side electrode.

2. A method of manufacturing a gas sensing element comprising a solid electrolytic body, a reference gas side electrode provided on a surface of said solid electrolytic body so as to be exposed to a reference gas, and a measured gas side electrode provided on another surface of said solid electrolytic body so as to be exposed to a measured gas, said manufacturing method comprising:

providing a fine-grain nucleus of noble metal on an electrode forming portion of said solid electrolytic body;

irradiating a laser beam to said fine-grain nucleus;

forming an unbaked film electrode on said fine-grain nucleus; and baking said film electrode in a reducing atmosphere to form said measured gas side electrode thereby providing a crystal face strength ratio of said measured gas side electrode according to X-ray diffraction satisfies the following relationship $$0.7 \leq \{I(200)/I(111)\} \text{ or } 0.6 \leq \{I(220)/I(111)\}$$

where I(200) represents the intensity of an X-ray diffraction measurement for a crystal face (200) of said measured gas side electrode, I(111) represents the intensity of an X-ray diffraction measurement for a crystal face (111) of said measured gas side electrode and I(220) represents the intensity of an X-ray diffraction measurement for a crystal face (220) of said measured gas side electrode.

3. A method of manufacturing a gas sensing element comprising a solid electrolytic body, a reference gas side electrode provided on a surface of said solid electrolytic body so as to be exposed to a reference gas, and a measured gas side electrode provided on another surface of said solid electrolytic body so as to be exposed to a measured gas, said manufacturing method comprising:

preparing a paste of fine-grain nucleus of noble metal applied crystal face orientation processing beforehand;

forming an unbaked film electrode by coating said paste on an electrode forming portion of said solid electrolytic body; and baking said film electrode in a reducing atmosphere to form said measured gas side electrode thereby providing a crystal face strength ratio of said measured gas side electrode according to X-ray diffraction satisfies the following relationship $$0.7 \leq \{I(200)/I(111)\} \text{ or } 0.6 \leq \{I(220)/I(111)\}$$

where I(200) represents the intensity of an X-ray diffraction measurement for a crystal face (200) of said measured gas side electrode, I(111) represents the intensity of an X-ray diffraction measurement for a crystal face (111) of said measured gas side electrode and I(220) represents the intensity of an X-ray diffraction measurement for a crystal face (220) of said measured gas side electrode.

4. A method of manufacturing a gas sensing element comprising a solid electrolytic body, a reference gas side electrode provided on a surface of said solid electrolytic body so as to be exposed to a reference gas, and a measured gas side electrode provided on another surface of said solid electrolytic body so as to be exposed to a measured gas, said manufacturing method comprising:

providing a fine-grain nucleus of noble metal on an electrode forming portion of said solid electrolytic body;

applying a reducing heat treatment to said fine-grain nucleus;

forming an unbaked film electrode on said fine-grain nucleus; and baking said film electrode in a reducing atmosphere to form said measured gas side electrode thereby providing a crystal face strength ratio of said measured gas side electrode according to X-ray diffraction satisfies the following relationship $$1.3 \leq \{I(200)+I(200)\}/I(111)$$

where I(200) represents the intensity of an X-ray diffraction measurement for a crystal face (200) of said measured gas side electrode, I(220) represents the intensity of an X-ray diffraction measurement for a crystal face (220) of said measured gas side electrode, and I(111) represents the intensity of an X-ray diffraction measurement for a crystal face (111) of said measured gas side electrode.

5. A method of manufacturing a gas sensing element comprising a solid electrolytic body, a reference gas side electrode provided on a surface of said solid electrolytic body so as to be exposed to a reference gas, and a measured gas side electrode provided on another surface of said solid electrolytic body so as to be exposed to a measured gas, said manufacturing method comprising:

providing a fine-grain nucleus of noble metal on an electrode forming portion of said solid electrolytic body;

irradiating a laser beam to said fine-grain nucleus;

forming an unbaked film electrode on said fine-grain nucleus; and baking said film electrode in a reducing atmosphere to form said measured gas side electrode thereby providing a crystal face strength ratio of said measured gas side electrode according to X-ray diffraction satisfies the following relationship $$1.3 \leq \{I(200)+I(200)\}/I(111)$$

where I(200) represents the intensity of an X-ray diffraction measurement for a crystal face (200) of said measured gas side electrode, I(220) represents the intensity of an X-ray diffraction measurement for a crystal face (220) of said measured gas side electrode, and I(111) represents the intensity of an X-ray diffraction measurement for a crystal face (111) of said measured gas side electrode.

6. A method of manufacturing a gas sensing element comprising a solid electrolytic body, a reference gas side electrode provided on a surface of said solid electrolytic body so as to be exposed to a reference gas, and a measured gas side electrode provided on another surface of said solid electrolytic body so as to be exposed to a measured gas, said manufacturing method comprising:

preparing a paste of fine-grain nucleus of noble metal applied crystal face orientation processing beforehand;

forming an unbaked film electrode by coating said paste on an electrode forming portion of said solid electrolytic body; and baking said film electrode in a reducing atmosphere to form said measured gas side electrode thereby providing a crystal face strength ratio of said measured gas side electrode according to X-ray diffraction satisfies the following relationship $$1.3 \leq \{I(200)+I(220)\}/I(111)$$

where I(200) represents the intensity of an X-ray diffraction measurement for a crystal face (200) of said measured gas side electrode, I(220) represents the intensity of an X-ray diffraction measurement for a crystal face (220) of said measured gas side electrode, and I(111) represents the intensity of an X-ray diffraction measurement for a crystal face (111) of said measured gas side electrode.

* * * * *